US00PP25333P3

(12) United States Plant Patent
Schoone

(10) Patent No.: US PP25,333 P3
(45) Date of Patent: Mar. 10, 2015

(54) *PHALAENOPSIS* ORCHID PLANT NAMED 'DREAM'

(50) Latin Name: ***Phalaenopsis* hybrid**
Varietal Denomination: Dream

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 174 days.

(21) Appl. No.: 13/573,497

(22) Filed: Sep. 19, 2012

(65) Prior Publication Data

US 2013/0081166 P1 Mar. 28, 2013

Related U.S. Application Data

(60) Provisional application No. 61/540,324, filed on Sep. 28, 2011.

(30) Foreign Application Priority Data

Sep. 30, 2011 (NL) ..... PBR OPS856

(51) Int. Cl.
*A01H 5/00* (2006.01)
*A01H 5/02* (2006.01)

(52) U.S. Cl.
CPC ..... *A01H 5/02* (2013.01)
USPC ..... Plt./311

(58) Field of Classification Search
CPC ..... A01H 5/02
USPC ..... Plt./311
See application file for complete search history.

(56) References Cited

U.S. PATENT DOCUMENTS

PP13,088 P2 * 10/2002 Glancy ..... Plt./311

* cited by examiner

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'Dream' particularly characterized by flowers which are pink/purple with some spots; the labellum is red/purple with some yellow and the column is purple/violet with white edges; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Dream'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Dream'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Dream' is a product of a controlled breeding program conducted by the inventors, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Dream' originated from a cross made by the inventor in 1999 in Strengweg, Heemskerk, The Netherlands. The female or seed parent is the *Phalaenopsis* cultivar designated 'Sexy Pink', unpatented. The male or pollen parent is the *Phalaenopsis* cultivar designated 'Firebird Jasmin', unpatented. The new *Phalaenopsis* 'Dream' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in July, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Dream', which in combination distinguish this *Phalaenopsis* as a new and distinct cultivar:

1. flowers which are purple/violet with some spots; the labellum is red/purple with some yellow and some white in the column;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Dream', the female parent 'Sexy Pink' has white flowers with dark purple/violet spots and a wide pink edge. They are about 7 cm in size. The male parent 'Firebird Jasmin' has dark red/purple colored flowers with white in the center with red/purple spots. They are about 11 cm in size. Whereas the flowers of 'Dream' are purple/violet and white with darker purple/violet marks. They are about 9 cm in size.

Presently, the commercial cultivar to which 'Dream' can be meaningfully compared is 'Jazz' (U.S. application Ser. No. 13/998,017). The flowers of 'Dream' are purple/violet and white with darker purple/violet marks, whereas the flowers of 'Jazz' are red/purple with purple/violet veins and at the base white.

BRIEF DESCRIPTION OF THE PHOTOGRAPHS

The accompanying photographs illustrate the overall appearance of the new *Phalaenopsis* 'Dream' showing the colors as true as is reasonably possible with colored reproductions of this type. Colors in the photographs may differ slightly from the color values cited in the detailed botanical description, which accurately describe the color of 'Dream'.

DETAILED BOTANICAL DESCRIPTION

Figure 1:
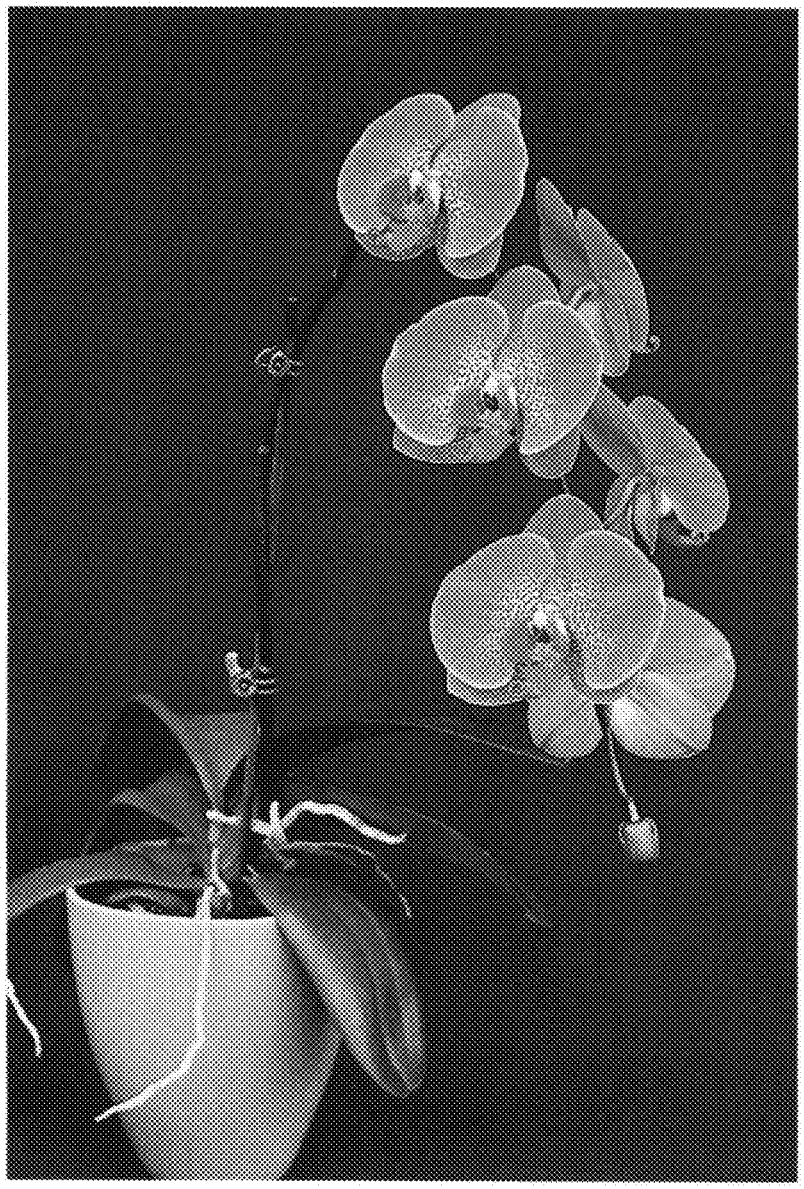
FIG. 1 shows a side view perspective of a typical flowering plant of 'Dream' in a 12 cm pot, at 16 months of age.

The new *Phalaenopsis* cultivar 'Dream' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Dream' as grown in a greenhouse in Strengweg, Heemskerk, The Netherlands, under conditions which closely approximate those generally used in commercial practice. Initially, the ideal temperature to grow plants of 'Dream' is 27° C. during the day and at night. Then, during the flowering phase of 'Dream', the ideal growing temperature is 20-22° C. during the day and 18° C. at night. Light levels for growing 'Dream' are a minimum of 5,000 lux and a maximum of 10,000 lux. A balanced fertilizer with level of 200 ppm N, 87 ppm P, 168 ppm K is applied. Duration of growth of 'Dream' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Dream' plants described is 12 months after potting.

Classification:

*Botanical.*—*Phalaenopsis* hybrid.

Parentage:

*Female or seed parent.*—*Phalaenopsis* cultivar designated 'Sexy Pink', unpatented.

*Male or pollen parent.*—*Phalaenopsis* cultivar designated 'Firebird Jasmin', unpatented.

Propagation:

*Type.*—tissue culture.

*Rooting habit and description.*—Fleshy; approximately 4 mm-7 mm wide and green/yellow in color (RHS 147B); freely branching. It takes 12 weeks for plants growing in tissue culture to initiate roots.

Plant:

*Size at maturity.*—Height (from bottom of pot to highest flower): about 54 to 58 cm. Spread: about 43 to 58 cm.

*Growth habit.*—Standard; green (RHS N139A) leaves and relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1 to 2 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, tip is blunt and asymmetric.

*Texture* (*both surfaces*).—Smooth and leathery.

*Margin.*—Entire.

*Base.*—Acute.

*Pubescence.*—None.

*Mature leaf length.*—About 17 to 21 cm.

*Mature leaf width.*—About 8 to 11 cm.

*Mature leaf thickness.*—About 1.5 mm.

*Mature leaf color* (*upper surface*).—RHS N139A.

*Mature leaf color* (*under surface*).—RHS N137C with purple (RHS N79A) on the edges and some purple marks (RHS N79A).

*Venation.*—Pattern: parallel. Color of midvein: upper surface: RHS 139A, under surface: RHS 79A.

Raceme:

*Quantity per plant.*—About 1 to 2.

*Number of flowers per raceme.*—About 4 to 8.

*Length.*—About 65 to 75 cm.

*Diameter.*—About 5 to 7 mm.

*Strength.*—Strong.

*Aspect.*—Upright.

*Texture.*—Glabrous and smooth.

*Color.*—RHS N187A.

*Internode.*—Length: about 30 to 40 mm.

Inflorescence description:

*Appearance*.—Upright to slightly pendant, racemose inflorescence with bilaterally symmetrical flowers that open in succession beginning with the lowermost flower.

*Buds*.—Height (from base to tip): about 15 to 25 mm. Diameter (at midpoint): about 12 to 22 mm. Shape: egg-shaped. Color: yellow/green RHS 145B and purple/violet RHS N81A.

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 1 to 2 racemes appear with about 4 to 8 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
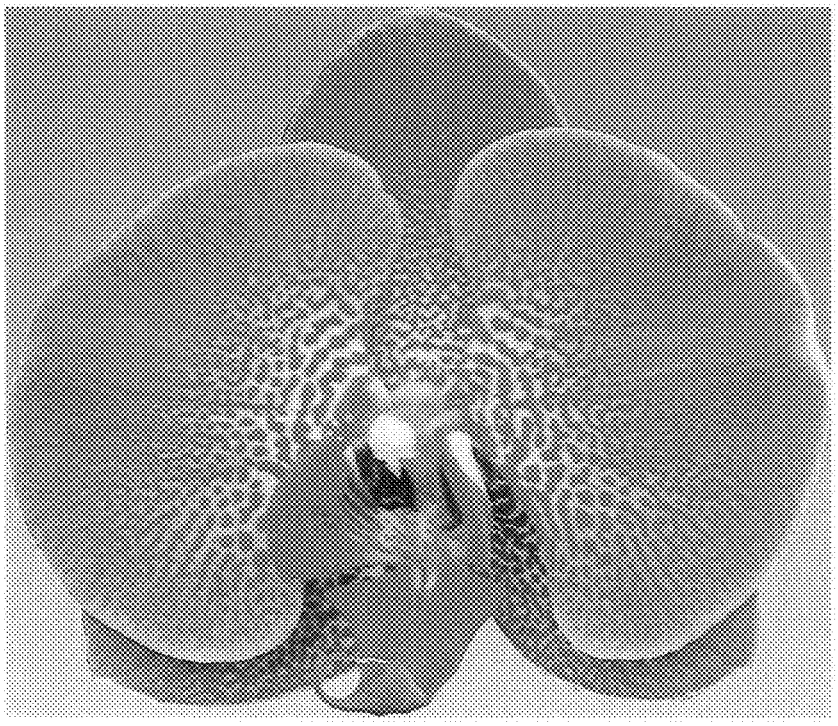
FIG. 2 shows a close-up view of a typical flower of 'Dream'.
Figure 3:
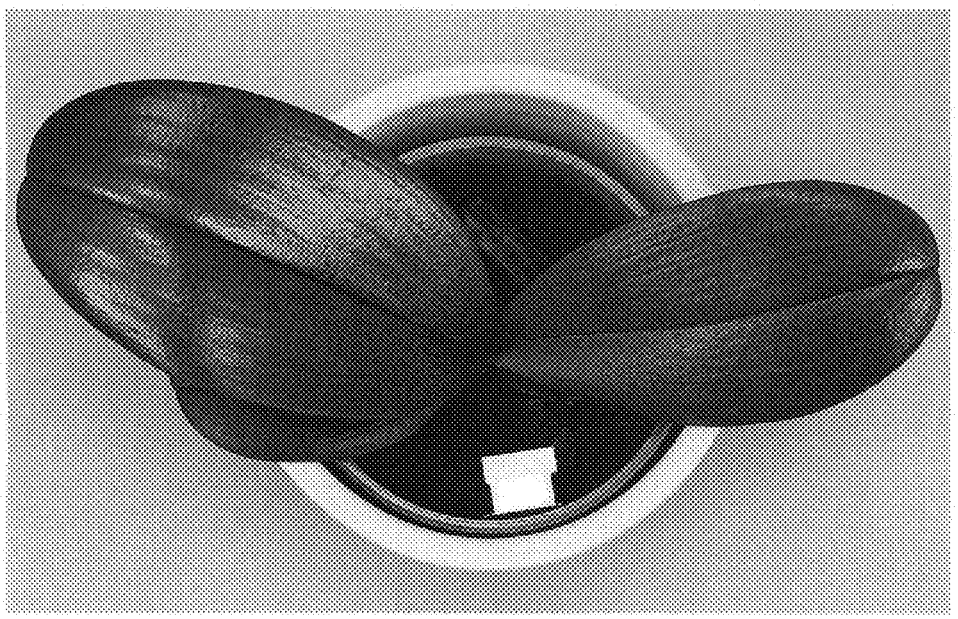
FIG. 3 shows a close-up view of the typical leaves of 'Dream'.

*Flower*.—Rate of opening: Flowers fully opened about 2 to 3 days after petal and sepal separation. Orientation at opening: slanted upward and outward. Shape: Typical shape of Phalaenopsis orchid; see FIG. 2. Size (of single bloom): Height: about 81 mm. Diameter: about 90 mm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and labellum. 2 lateral petals: Overall shape: broadly ovate and weakly cupped. Apex: oval. Margin: entire and weakly undulate. Base: broadly ovate. Length: about 55 to 60 mm. Width: about 40 mm. Texture: Upper surface: smooth and satiny. Under surface: smooth and satiny. Color (when fully opened): the upper surface at the base is purple/violet (RHS N80C) and white (RHS NN155C) with purple/violet marks (RHS N80A). Towards the middle to the edge the color is purple/violet (RHS N80B) with darker purple/violet marks (RHS N80A) and a white margin (RHS N155B). At the base of the under surface some white (RHS NN155C) and purple/violet (RHS N80B). Veins are purple/violet (RHS N80A). Labellum: Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it. Margin (both midlobe and lateral lobes): entire and weakly undulate. Length midlobe: about 24 mm. Width (not flattened) midlobe: about 24 mm. Depth of tube (made from lateral lobes): about 10 mm. Length lateral lobe (not flattened): about 16 mm. Width: about 9 mm. Texture: Upper & under surface (both midlobe and lateral lobes): smooth and satiny. Color (when fully opened): Main color midlobe upper surface is red/purple (RHS 59A) with a haze of RHS N78A. At the base a little yellow (RHS 7B) and a line in the center (RHS N79A). Main color lateral lobes is RHS 79C. At the base yellow (RHS 5A) and white (RHS NN155C) and some stripes (RHS N79B). The under surface of the midlobe is RHS N78A and small edges of RHS 59A. The under surface of lateral lobes RHS N81A and RHS NN155C. Cirrhi (filiform appendages at the apex): medium (about 10 mm). Color: RHS 59A and N79B and the tip is RHS 7B. Pestle (callosities): Length: about 6 mm. Width (not flattened): about 7 mm. Height: about 9 mm. Color: Main color is yellow/orange (RHS 17A). Stripes and spots are red/purple (RHS 59A).

*Sepals*.—Arrangement: Outer whorl comprises 3 sepals. Overall shape: elliptical and weakly cupped. Length: about 40 to 50 mm. Width: about 35 mm. Margin: entire and weakly undulate. Apex: oval. Base: broadly ovate. Texture: Upper & under surface: smooth and satiny. Color (when fully opened): Upper surface: Main color dorsal sepal is purple (RHS N78A) with purple/violet at the base (RHS N80B) and purple stripes (RHS N81A) and spots (RHS N81A). Main color lateral sepal is RHS N78A with some stripes/spots (RHS N81A) and some white (RHS NN155B) on the lower half. Under surface: Dorsal sepal is purple (RHS 77B) with purple veins (RHS N79C), in the center a mark (RHS 71A) and some spots (RHS NN155B). The lateral sepal is red/purple (RHS 72A) with red/purple veins (RHS 71A). At the base some yellow/green (RHS 145B and some spots (RHs NN155B).

*Pedicel*.—Length: about 30 to 40 mm. Diameter: about 3 mm. Texture: glabrous and smooth. Color: Base: purple (RHS N77A), middle: red/purple (RHS 59A) with spots/stripes (RHS 151C), end: purple (RHS N78B).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 8 mm. Diameter: about 6 mm. Color: Main color is purple/violet (RHS N78A) and white edges (RHS NN155C).

*Pollinia*.—Quantity: Two. Size: about 1 mm. Color: orange RHS 24 A.

*Ovary*.—Length: about 3 mm. Diameter: about 4 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Dream', as illustrated and described herein.

* * * * *